(12) United States Patent
Jostock et al.

(10) Patent No.: US 9,315,844 B2
(45) Date of Patent: *Apr. 19, 2016

(54) METHODS FOR SELECTING EUKARYOTIC CELLS EXPRESSING A HETEROLOGOUS PROTEIN

(71) Applicants: Thomas Jostock, Neuenburg am Rhein (DE); Hans-Peter Knopf, Schallstadt (DE)

(72) Inventors: Thomas Jostock, Neuenburg am Rhein (DE); Hans-Peter Knopf, Schallstadt (DE)

(73) Assignee: NOVARTIS AG, Basel (CH)

( * ) Notice: Subject to any disclaimer, the term of this patent is extended or adjusted under 35 U.S.C. 154(b) by 11 days.

This patent is subject to a terminal disclaimer.

(21) Appl. No.: 14/174,228

(22) Filed: Feb. 6, 2014

(65) Prior Publication Data

US 2014/0154739 A1 Jun. 5, 2014

Related U.S. Application Data

(62) Division of application No. 13/203,546, filed as application No. PCT/EP2010/001223 on Feb. 26, 2010, now Pat. No. 8,962,274.

(30) Foreign Application Priority Data

Feb. 27, 2009 (EP) ..................... 09154000

(51) Int. Cl.
| | |
|---|---|
| *C12P 21/06* | (2006.01) |
| *C12N 1/20* | (2006.01) |
| *C12N 15/00* | (2006.01) |
| *C07K 16/18* | (2006.01) |
| *C07K 16/00* | (2006.01) |
| *C12P 21/00* | (2006.01) |
| *C12N 15/67* | (2006.01) |
| *C12N 15/85* | (2006.01) |

(52) U.S. Cl.
CPC ................. *C12P 21/00* (2013.01); *C07K 16/00* (2013.01); *C07K 16/18* (2013.01); *C12N 15/67* (2013.01); *C12N 15/85* (2013.01)

(58) Field of Classification Search
CPC ........ C12P 21/00; C12N 15/67; C12N 15/85; C07K 16/00; C07K 16/18
USPC ....................................... 435/69.1
See application file for complete search history.

(56) References Cited

U.S. PATENT DOCUMENTS

| 5,316,938 A | 5/1994 | Keen et al. |
| 7,935,808 B2 | 5/2011 | Gion et al. |
| 2008/0241883 A1 | 10/2008 | Gion et al. |

FOREIGN PATENT DOCUMENTS

| EP | 0246049 | 11/1987 |
| EP | 1221476 A2 | 10/2002 |
| EP | 1953222 A1 | 8/2008 |
| JP | 2001037478 A2 | 2/2001 |
| RU | 2209211 C2 | 7/2003 |
| WO | 9103554 | 3/1991 |
| WO | 98/04718 A1 | 2/1998 |
| WO | 02/22805 A2 | 3/2002 |
| WO | 03/045995 A2 | 6/2003 |

OTHER PUBLICATIONS

"Iscove's Modified Dulbecco's Medium". sTEMcELL tECHNOLOGIES, dOCUMENT # 29841. www.stemcell.com 2014.
Jiang Zhou et al: "Regulation of recombinant monoclonal antibody production in Chinese hamster ovary cells: a comparative study of gene copy number, mRNA level, and protein expression", Biotechnology Progress, val. 22, No. 1, pp. 313-318, 2006.
Mayer-Kuckuk Philipp et al: "Cells exposed to antifolates show increased cellular levels of proteins fused to dihydrofolate reductase: a method to modulate gene expression", Proceedings of the National Academy of Sciences of the United States of America, vol. 99, No. 6, pp. 3400-3405, 2002.
Zhu Wei-Yong et al: "Severe folate restrictions results in depletion of and alteration in the composition of the intracellular folate pool, moderate sensitization to methotrexate and trimetrexate, upregulation of endogenous DHFR activity, and overexpression of metallothionein II and folate receptor alpha that, upon folate" Journal of Experimental Therapeutics & Oncology 2002 Sep.-Oct. val. 2, No. 5, pp. 264-277, 2002.
Santos et al: "Methotrexate gamma-hydroxamate derivatives as potential dual target antitumor drugs" Bioorganic & Medicinal Chemistry, Pergamon, GB LNKD_DOI:10.1016/J.DMC.2006.11. 017, vol. 15, No. 3, pp. 1266-1274, 2007.
Etienne M-C et al: "Combination of reduced folates with methotrexate or 5-fluorouracil- comparison between 5-formyltetrahydrofolate (folinic acid) and 5-methyltetrahydrofolate in vitro activities", Biochemical Pharmacology, Pergamon, Oxford, GB LNKD-001:10. 1016/006-2952(93)90581-G, vol. 46, No. 10, pp. 1767-1774, 1993.
Backus H H Jet al: "Folate depletion increases sensitivity of solid tumor cell lines to 5-fluorouracil and antifolates", International Journal of Cancer, vol. 87, No. 6, pp. 771-778, 2000.
Grillari J et al: "Analysis of alternations in gene expression after amplification of recombinant genes in CHO cells", Journal of Biotechnol. 87, pp. 59-65, 2001.
Levitt N et al: "Definition of an efficient synthetic poly(A) site", Genes & Development 3(7), pp. 1019-1025, 1989.
Sub Raman I S et al: "Expression of the mouse dihydrofolate reductase complementary deoxyribonucleic acid in simian virus 40 vectors", Molecular and Cellular Biology, 1(9), pp. 854-864, 1981.
Eaton D et al: "Construction and characterization of an active factor viii variant lacking the central one-third of the molecule", Biochemistry 25(26), pp. 8343-8347, 1986.

(Continued)

*Primary Examiner* — Maryam Monshipouri
(74) *Attorney, Agent, or Firm* — James Lynch

(57) ABSTRACT

The present invention pertains to a method for selecting at least one eukaryotic host cell expressing a product of interest. The method entails providing a plurality of host cells which are dependent upon folate uptake and contain polynucleotides encoding for the product of interest and a DHFR enzyme. The cells are cultured in a selective culture medium containing at least an inhibitor of DHFR and folate. The expressed cells are then selected.

15 Claims, No Drawings

(56) References Cited

OTHER PUBLICATIONS

Neuberger M: "Expression and regulation of immunoglobulin heavy chain gene transfected into lymphoid cells", The EMBO Journal 2(8), pp. 1373-1378, 1983.

Oumard A et al: "Recommended method for chromosome exploitation: RMCE-based cassette-exchange systems in animal cell biotechnology", Cytotechnology 50, pp. 93-108, 2006.

Sorrell D et al: Targeted modification of mammalian genomes, Biotechnology Advances 22, pp. 431-469, D 2005.

Wurm F: "Production of recombinant protein therapeutics in cultivated mammalian cells", Nature Biotechnology 22 D (11) pp. 1393-1398, 2004.

METHODS FOR SELECTING EUKARYOTIC CELLS EXPRESSING A HETEROLOGOUS PROTEIN

FIELD OF THE INVENTION

The present invention relates to a novel method of selecting eukaryotic host cells, in particular mammalian host cells, expressing a product of interest. Furthermore, the present invention pertains to a method for efficiently producing a product of interest with a high yield.

BACKGROUND OF THE INVENTION

The ability to clone and express products of interest such as recombinant peptides and proteins in large amounts has become increasingly important. The ability to purify high levels of proteins is important in the human pharmaceutical and biotechnological field, for example for producing protein pharmaceuticals as well as in the basic research setting, for example for crystallizing proteins to allow the determination of their three dimensional structure. Proteins that are otherwise difficult to obtain in quantity can be over-expressed in a host cell and subsequently isolated and purified.

The choice of an expression system for the production of recombinant proteins depends on many factors, including cell growth characteristics, expression levels, intracellular and extracellular expression, post-translational modifications and biological activity of the protein of interest, as well as regulatory issues and economic considerations in the production of therapeutic proteins. Key advantages of mammalian cells over other expression systems such as bacteria or yeast are the ability to carry out proper protein folding, complex N-linked glycosylation and authentic O-linked glycosylation, as well as a broad spectrum of other post-translational modifications. Due to the described advantages, eukaryotic and in particular mammalian cells are currently the expression system of choice for producing complex therapeutic proteins such as monoclonal antibodies.

The most common approach to obtain high expressing host cells (also called high producers) generates an appropriate expression vector for expressing the product of interest as a first step. The expression vector drives the expression of the polynucleotide encoding the product of interest in the host cell and provides at least one selectable marker for generating the recombinant cell line. Key elements of mammalian expression vectors usually include a constitutive or inducible promoter capable of robust transcriptional activity; optimized mRNA processing and translational signals that usually include a Kozak sequence, a translation termination codon, mRNA cleavage and polyadenylation signals, a transcription terminator and selectable markers for the preparation of stable cell lines and for gene amplification; furthermore a prokaryotic origin of replication and selectable markers for vector propagation in bacteria can be provided by the expression vector.

In recent years the focus of development was concentrating on the design of improved vectors for gene expression in host cells. Despite of the plethora of available vectors, however, robust polypeptide/protein production with a high yield in mammalian cells is still challenging.

One established procedure for obtaining high producing cell lines expressing the product of interest with high yield is the stable transfection of the host cells. However, the stable integration into the genome is a rare event and only a small subset of stably transfected cells are high producers. Their selection is accordingly challenging.

Selectable markers and selection systems are widely used in genetic engineering, recombinant DNA technology and the production of recombinant products in order to obtain host cells expressing the product of interest with high yield. Respective systems are also useful to generate and identify stably transfected clones. The primary goal of using respective selectable markers and selection systems is to introduce a selectable gene which upon exposure to selective growth conditions allows the identification of cells capable of high-level production of the introduced selectable marker and accordingly, the recombinant product of interest. Increasing the yield of product expression can be e.g. achieved by gene amplification using cells lines e.g. deficient in an enzyme such as dihydrofolate reductase (DHFR) or glutamine synthetase (GS) in conjunction with expression vectors containing genes encoding these selectable marker enzymes and agents such as methotrexate (MTX), which inhibits DHFR, and methionine sulfoxamine (MSX) which inhibits GS.

One prominent selection system which is commonly used in the prior art is the dihydrofolate reductase/MTX selection system. Dihydrofolate reductase (DHFR) catalyzes the NADP-dependent reduction of dihydrofolic acid to tetrahydrofolic acid (THF). THF is then intraconverted to 10-formyl-DHF and 5,10-methylene-DHF which are used in the de novo biosynthesis of purines and thymidylate, respectively. DHF is the byproduct of the catalytic activity of thymidylate synthase (TS) which catalyzes the convertion of dUMP to dTMP in a 5,10-methylene-THF dependent reaction. Thus, DHFR is crucial for the recycling of THF cofactors that are essential for the biosynthesis of purine and pyrimidine nucleotides that are neccassary for the DNA replication. Hence, cells (for example CHO cells) that lack the DHFR gene (i.e. by targeted genomic deletion) can be used as recipients for the transfection of the DHFR gene in a medium that is free of nucleotides. After transfection, the cells can be subjected to gradual increase in the concentrations of the antifolate MTX, a most potent DHFR inhibitor (Kd=1 pM), thereby forcing the cells to produce increased levels of DHFR. After multiple rounds of selection, the selectable marker DHFR frequently undergoes significant amplification. Also more sensitive mutant forms of the respective selectable markers can be used in conjunction with wildtype host cells. Alternatively, a mutant mouse DHFR with a major resistance, i.e. less sensitivity, to MTX or other mutant forms of DHFR has also been extensively used as a dominant selectable marker that markley enhanced the acquisition of high level MTX-resistance in transfected cells. However, a major disadvantage of the DHFR/MTX selection system used in the prior art is that this technique utilizes a mutagenic cytotoxic agent, MTX, that can particularly in higher concentrations alter the genotype of the recipients cells. This frequently results in MTX-resistant cell populations in which no expression of the target gene of interest is present due to loss of function mutations for example in the reduced folate carrier (RFC)/or loss of RFC gene expression, both of which abolish MTX uptake. However, increasing/high concentrations of MTX are necessary, in order to achieve sufficiently stringent selection conditions in order to isolate host cells producing the product of interest with a sufficient yield.

As becomes apparent, a high stringency selection system is crucial to enrich high producing cells from a transfected population. The higher the stringency of the selection system the lower the number of low producers after the selection process and the higher the chance to find the very rare ultra high producing clones in a transfected cell population.

Therefore, it is the object of the present invention to provide a stringent selection system for selecting host cells producing a product of interest with high yield, as well as methods for producing a product of interest with sufficient yield. In particular, it is the object of the present invention to provide a stringent selection system which requires less amounts of toxic agents, in particular MTX. Furthermore, it is the object of the present invention to provide a method for producing a product of interest with a high yield.

SUMMARY OF THE INVENTION

The present invention pertains to a selection system for selecting host cells expressing a product of interest with a high yield and to the production of respective products, in particular polypeptides such as antibodies.

According to one aspect, the present invention pertains to a method for selecting at least one eukaryotic host cell expressing a product of interest, said method comprising at least the following steps:
  (a) providing a plurality of eukaryotic host cells, wherein the cellular viability of said host cells is dependent upon folate uptake, wherein said eukaryotic host cells comprise at least
    (i) an introduced polynucleotide encoding a product of interest and
    (ii) an introduced polynucleotide encoding a DHFR enzyme;
  (b) culturing said plurality of eukaryotic host cells in a selective culture medium comprising at least an inhibitor of DHFR and folate in a limiting concentration;
  (c) selecting at least one eukaryotic host cell expressing the product of interest.

The invention also relates to a process for producing a product of interest, comprising culturing a host cell selected according to the present invention under conditions that allow for the expression of the product of interest.

Also provided is a selective culture medium, comprising at least an inhibitor of DHFR and folate in a limiting concentration which can be used in the selection method according to the present invention. A "selective culture medium" is a cell culture medium useful for the selection of host cells.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

The present invention pertains to a selection system using DHFR as a selectable marker, which requires a lower concentration of toxic agents such as the antifolate MTX but still provides stringent selection conditions sufficient for identifying high producing host cells.

According to one aspect of the present invention, a method for selecting at least one eukaryotic host cell expressing a product of interest is provided, said method comprising at least the following steps:
  (a) providing a plurality of eukaryotic host cells, wherein cellular viability of said host cells is dependent upon folate uptake, wherein said eukaryotic host cells comprise at least
    (i) an introduced polynucleotide encoding a product of interest and
    (ii) an introduced polynucleotide encoding a DHFR enzyme;
  (b) culturing said plurality of eukaryotic host cells in a selective culture medium comprising at least an inhibitor of DHFR and folate in a limiting concentration;
  (c) selecting at least one eukaryotic host cell expressing the product of interest.

A "polynucleotide" is a polymer of nucleotides which are usually linked from one deoxyribose or ribose to another and refers to DNA as well as RNA, depending on the context. The term "polynucleotide" does not comprise any size restrictions and also encompasses polynucleotides comprising modifications, in particular modified nucleotides.

A "product of interest" refers to the product to be expressed from said host cell. The product of interest may be e.g. a polypeptide or a polynucleotide, such as RNA. Preferably, the product of interest is a polypeptide, in particular an immunoglobulin molecule. Further examples of products of interest are described in detail below.

An "introduced polynucleotide" refers to a polynucleotide sequence that has been introduced into a host cell e.g. by the use of recombinant techniques such as transfection. The host cell may or may not comprise an endogenous polynucleotide corresponding respectively being identical to the introduced polynucleotide. Introduction may be achieved e.g. by transfecting a suitable vector that may integrate into the genome of the host cell (stable transfection). Suitable expression vectors allowing the introduction of polynucleotides into the host cell are described in detail below. In case the heterologous nucleic acid is not inserted into the genome, the heterologous nucleic acid can be lost at the later stage e.g. when the cells undergo mitosis (transient transfection). Suitable vectors might also be maintained in the host cell without integrating into the genome, e.g. by episomal replication. However, also other techniques are known in the prior art for introducing a polynucleotide into a host cell which are described in further detail below.

An "inhibitor of DHFR" is a compound which inhibits the activity of the dihydrofolate reductase (DHFR). A respective inhibitor may for example compete with the DHFR substrate for binding to DHFR. Suitable DHFR inhibitors are for example antifolates such as methotrexate (MTX). Further examples include but are not limited to trimetrexate glucuronate (neutrexine), trimethoprim, pyrimethamine and pemetrexed.

The term "selecting" or "selection" as used herein, in particular refers to a process of using a selectable marker and selective culturing conditions to select and accordingly obtain host cells that have incorporated the vector or vector combination according to the present invention. Thereby, successfully transfected host cells can be isolated and/or enriched from the population of transfected host cells.

Host cells that have not successfully incorporated the vector or vector combination according to the present invention preferably die or are impaired in growth under the selective culture conditions compared to host cells that have successfully incorporated the vector or vector combination according to the present invention. During selection, host cells which have successfully incorporated the vector or vector combination according to the present invention can be enriched as pool from the population of transfected host cells. Also individual host cells can be isolated from the population of transfected host cells during selection (e.g. by clonal selection). Suitable embodiments of selection procedures in order to obtain successfully transfected host cells (e.g. by FACS sorting or limited dilution) are well known in the prior art and accordingly, need no detailed description.

A "limiting concentration of folate" refers to a concentration of folates in the selective culture medium which provides a selective pressure on the host cell. Accordingly, folates are not comprised in the selective culture medium in affluence, thereby providing a selection pressure on the host cells. The folate comprised in the selective culture medium in a limiting concentration is capable of being taken up into and being processed by the host cell. Folates and in particular derivatives of folate which would not be processed by the host cell would not contribute to the selection pressure and accordingly would not contribute to the limiting concentration. Suitable concentration ranges are described below.

A "polypeptide" refers to a molecule comprising a polymer of amino acids linked together by a peptide bond(s). Polypeptides include polypeptides of any length, including proteins (for example, having more than 50 amino acids) and peptides (for example, having 2-49 amino acids). Polypeptides include proteins and/or peptides of any activity or bioactivity. Suitable examples are outlined below.

It was surprisingly found that a selection system for providing recombinant eukaryotic cells capable of producing a product of interest can be based on the limited availability of folates in the selective culture medium in conjunction with the use of DHFR as selectable marker. The system is widely applicable, i.e. to eukaryotic host cells which cellular viability depends on the uptake of folate. As is described above, the prior art must use rather high antifolate/MTX concentrations in order to achieve a sufficient selection pressure for gene amplification and accordingly, to achieve an increase in the production of the product of interest. This is a disadvantage as antifolates such as MTX are toxic and may genetically alter the host cell. The approach of the present invention which is based on the combined use of a DHFR selection marker with a limiting concentration of folates in the selective culture medium has the advantage that the selection stringency is considerable increased even at low DHFR inhibitor concentrations. Thus, when using the selection system of the present invention, high producers are obtained even when using at low concentrations of the DHFR inhibitor (for example MTX) in the selective culture medium. Thus, less DHFR inhibitor and accordingly less toxic agent concentrations are needed when using the teaching of the present invention compared to the approaches of the prior art for providing stringent selection conditions that allow the identification of high producing cell clones. Due to its unique design, a very stringent selection system is provided allowing the enrichment of high producing cells from the transfected host cell population. This high stringency of the selection system according to the present invention lowers the number of low producers in the population after selection in the population and increases the chance to find the very rare ultrahigh producing clones.

The selective culture medium may comprise one or more types of folate. A folate according to the present invention can e.g. be an oxidized folate (i.e. folic acid) or a reduced folate or a derivative thereof. In general, a folate may be useful within the present invention as long as such folate will be capable of being taken up into a eukaryotic cell preferably by a functional membrane-bound folate receptor. The oxidized folate, i.e. folic acid, as well as reduced derivatives of folic acid, known as reduced folates or tetrahydrofolates (THF), are a group of B-9 vitamins that are essential cofactors and/or coenzymes for the biosynthesis of purines, thymidylate and certain amino acids in eukaryotic, in particular mammalian, cells. THF cofactors are particularly crucial for DNA replication and hence cellular proliferation.

Specifically, THF cofactors function as donors of one-carbon units in a series of interconnected metabolic pathways involving de novo biosynthesis of purines and thymidylate, amino acids as well as methyl group metabolism, including CpG island methylation of DNA. Specifically, THF cofactors including 10-formyl-THF (10-CHO-THF) contribute one-carbon units in two key de novo formyltransferase reactions involved in the de novo biosynthesis of purines. A preferred example of an oxidized folate is folic acid. Preferred examples of reduced folates are 5-methyl-tetrahydrofolic acid, 5-formyl-tetrahydrofolic, 10-formyl-tetrahydrofolic acid and 5,10-methylene-tetrahydrofolic acid.

The concentration of folate in the selective medium depends in particular on the eukaryotic host cell used. A folate concentration of 500 nM or less, 250 nM or less, 150 nM or less, 100 nM or less, 75 nM or less, 50 nM or less, 25 nM or less, 15 nM or less or even 10 nM or less such as 7.5 nM or less is suitable. Suitable ranges include 0.1 nM-500 nM, 0.1 nM-250 nM, 5 or 10 nM-250 nM, preferably 1 nM-150 nM, 5 or 10 nM-150 nM, 1 nM-100 nM, 5 or 10 nM-100 nM and more preferred 1 nM-50 nM, 2.5 nM-50 nM, 10 nM-50 nM or 12.5 nM-50 nM. These concentrations are particularly suitable when using folic acid as folate.

Respective concentrations are limiting in the sense of the present invention and thus suitable to provide a selective pressure on the host cells. The lower the concentration the stronger is the exerted selection pressure as long as the cells are still viable. The described concentration ranges are particularly suitable for using CHO cells as host cells.

The concentration of the DHFR inhibitor used in the selective culture medium also depends on the eukaryotic host cell used. A DHFR inhibitor concentration of 500 nM or less, 400 nM or less, 300 nM or less, 250 nM or less, 200 nM or less, 150 nM or less is advantageous in case the concentration of the DHFR inhibitor in the selective medium is supposed to be reduced. However, preferably, the selective medium comprises at least 10 nM of the DHFR inhibitor. Preferred antifolate concentrations, preferably MTX, are 1 nM-500 nM, preferably 10 nM-200 nM, 10 nM-150 nM and more preferred 10 nM-100 nM. Respective concentrations in the selective culture medium are particularly suitable for CHO cells.

The preferred concentrations and concentration ranges of folate and antifolate described above can be combined with each other. According to one embodiment, a selective culture medium is used which comprises a concentration of DHFR inhibitor, preferably MTX, of 200 nM or less, preferably 150 nM or less, preferably 100 nM or less and a folate concentration, preferably folic acid, of less than 100 nM, preferably less than 75 nM. In one embodiment, a folate concentration of 12.5 nM-50 nM is used in combination with an antifolate concentration of 10 nM-100 nM. Preferably, folic acid and MTX are used as folate and antifolate.

The feasible concentrations of folic acid and MTX may be dependent from one another; a preferred combination is a concentration of folic acid at 2.5 nM-75 nM, 2.5 nM-50 nM or 12.5 nM-50 nM combined with a concentration of MTX at 10 nM-500 nM, preferably 10 nM-100 nM. These concentrations are particularly preferred when using a DHFR+ (plus) cell.

The concentrations described above are particularly suitable for fast growing suspension cells, which is a preferred phenotype for commercial production cell lines. However, different cell lines may have different folic acid consumption properties. Furthermore, the limiting/selective concentrations may vary depending on the used folate, respectively antifolate. Therefore, the limiting concentrations of folate, in particular folic acid and antifolate, in particular MTX as well as the suitable folic acid to MTX ratios may differ for different cell lines. Suitable concentrations, however, can easily be determined experimentally by the skilled person.

According to one embodiment, the host cells are pre-cultured in a folate free culture medium or in a culture medium comprising a limiting concentration of folate prior to transfection and/or selection. Suitable limiting concentrations of folate are described above. Preferably, said culture medium for pre-culturing the host cells comprises folate, in particular folic acid in a concentration of 50 nM or less.

The expression of the incorporated selectable marker DHFR provides a selective advantage under selective culture conditions to the host cells. E.g. host cells (e.g. CHO cells) that lack the DHFR gene (e.g. by targeted genomic deletion, also called DHFR⁻ host cells) can be used as recipients for the transfection of the DHFR gene as selectable marker gene in a medium that is free of nucleotides. However, it is also possible to use host cells that express DHFR endogenously (DHFR⁺ (plus) host cells) when performing a DHFR selection, if appropriate selective culture conditions are used. After transfection with the polynucleotides according to the present invention, the cells can be subjected to a gradual increase in the concentrations of inhibitors of DHFR. One example of DHFR inhibitors are antifolates such as MTX, which is a potent DHFR inhibitor (Kd=1 pM). The presence of the antifolate such as MTX in the medium forces the cells to produce increased levels of DHFR in order to survive. Upon multiple rounds of selection, the selectable marker DHFR frequently undergoes significant gene amplification in order to achieve that.

Several suitable DHFR genes are known in the prior art that can be used in conjunction with the present invention. The DHFR may be a wildtype DHFR or a functional variant or derivative thereof. The term a "variant" or "derivative" include DHFR enzymes having one or more amino acid sequence exchanges (e.g. deletions, substitutions or additions) with respect to the amino acid sequence of the respective DHFR enzyme, fusion proteins comprising a DHFR enzyme or functional fragment thereof and DHFR enzymes which have been modified to provide an additional structure and/or function, as well as functional fragments of the foregoing, which still have at least one function of a DHFR enzyme. DHFR enzymes/variants can be used as selection marker, which are more or less sensitive to MTX than the wildtype DHFR enzyme. According to one embodiment, the DHFR enzyme used is more sensitive for antifolates such as MTX than the corresponding wildtype DHFR enzyme and/or the DHFR enzyme endogenously expressed by the host cell if expressed. The DHFR enzyme can be derived from any species as long as it will be functional within the present invention, i.e. compatible with the host cell utilised. E.g., a mutant mouse DHFR with a major resistance to MTX has been extensively used as a dominant selectable marker that markedly enhances the acquisition of high level MTX-resistance in transfectant cells. Preferably, a DHFR enzyme is used which is less susceptible and thus less sensitive to a DHFR inhibitor such as MTX than the DHFR enzyme endogenously expressed in a DHFR⁺ (plus) host cell.

According to one embodiment, an intron or a fragment thereof is placed at the 3' end of the open reading frame of the DHFR gene. This has advantageous effects on the expression/amplification rate of the construct. The intron used in the DHFR expression cassette is leading to a smaller, non functional variant of the DHFR gene (Grillari et al., 2001, J. Biotechnol. 87, 59-65). Thereby the expression level of the DHFR gene is lowered and can thus further increase the stringency of the selection system. Accordingly, the host cell may comprise an introduced polynucleotide encoding a DHFR enzyme, said polynucleotide comprising an intron which is located 3' of the DHFR coding sequence. Alternative methods making use of an intron to reduce the expression level of the DHFR gene are described in EP 0 724 639 and could also be used.

In contrast to most prokaryotes, plants and fungi which synthesize their own folates, mammals and other eukaryotic species are devoid of THF cofactor biosynthesis and must therefore obtain them from exogenous sources, usually the culture medium. Three independent transport systems are currently known to mediate the uptake of folates and antifolates in mammalian cells, namely the reduced folate carrier (RFC); the proton-coupled folate transporter (PCFT, also known as SLC46A) and folate receptors (FRs).

The eukaryotic host cell is, preferably, selected from the group consisting of a mammalian cell, an insect cell, a plant cell and a fungi cell. Fungi cells and plant cells can be prototrophic for folates (i.e. such cells can autonomously synthesize their own folates necessary for their cellular viability, i.e. cellular growth and proliferation). The present invention encompasses in particular such fungi and plant cells which are or may become auxotrophic for folates. This may be for example due to genetic manipulation, i.e. cells are now unable to synthesize sufficient amounts of folates necessary for their cellular viability. For example, the capacity of such fungi or plant cells to endogenously biosynthesize folates, e.g. via an appropriate metabolic pathway, can be inactivated, e.g. by gene disruption or gene silencing of appropriate target genes, or inhibition of key enzymes, etc. Preferably, the host cell is a mammalian cell. Said mammalian cell can be selected from the group consisting of a rodent cell, a human cell and a monkey cell. Particularly preferred is a rodent cell, which preferably is selected from the group consisting of a CHO cell, a BHK cell, a NSO cell, a mouse 3T3 fibroblast cell, and a SP2/0 cell. A most particularly preferred rodent cell is a CHO cell. Also preferred is a human cell, which, preferably, is selected from the group consisting of a HEK293 cell, a MCF-7 cell, a PerC6 cell, and a HeLa cell. Further preferred is a monkey cell, which, preferably, is selected from the group consisting of a COS-1, a COS-7 cell and a Vero cell. The host cell is preferably a DHFR⁺ (plus) cell, in particular a DHFR⁺ (plus) CHO cell.

According to one embodiment, the polynucleotide encoding a product of interest and the polynucleotide encoding a DHFR enzyme were introduced by at least one expression vector. Suitable techniques for introducing a respective vector are described below and include e.g. transfection.

An "expression vector" according to the present invention is a polynucleotide capable of carrying at least one foreign nucleic acid fragment. A vector functions like a molecular carrier, delivering fragments of nucleic acids respectively polynucleotides into a host cell. It comprises at least one expression cassette comprising regulatory sequences for properly expressing a polynucleotide incorporated therein. Polynucleotides (e.g. encoding the product of interest or selectable markers) may be inserted into the expression cassette(s) of the expression vector in order to be expressed therefrom. The expression vector according to the present invention may be present in circular or linearized form. The term "expression vector" also comprises artificial chromosomes or similar respective polynucleotides allowing the transfer of foreign nucleic acid fragments.

The polynucleotide encoding the product of interest and the polynucleotide encoding the DHFR enzyme can be located on the same or different expression vectors. Using an expression vector carrying both polynucleotides has the advantage that only one expression vector needs to be introduced into the host cell. Furthermore, in particular when establishing a stable expression line it is more likely that the polynucleotides are integrated together into the genome and, accordingly, expressed with a similar yield. However, it is also possible and within the scope of the present invention to use a combination of at least two expression vectors for transfection, wherein the respective polynucleotides are located on different expression vectors. Said combination of expression vectors is then transfected into the host cell.

The eukaryotic host cell may comprise at least one additional introduced polynucleotide encoding a further product of interest. This embodiment is particularly suitable for expressing immunoglobulin molecules. According to a preferred embodiment, the host cell comprises at least two introduced polynucleotides each encoding a product of interest, wherein at least one polynucleotide encodes the heavy chain of an immunoglobulin molecule or a functional fragment thereof and the other polynucleotide encodes the light chain of an immunoglobulin molecule or a functional fragment thereof. The respective polynucleotides can be introduced by using an appropriate expression vector. Said polynucleotides encoding the heavy and light chain of an immunoglobulin molecule (or a functional fragment thereof) may be located on the same or on different expression vectors in case a combination of at least two expression vectors is used.

The host cell and accordingly the expression vector for introducing polynucleotides into said host cell may additionally comprise one or more further polynucleotide(s) encoding one or more additional selectable marker(s). Accordingly, in one embodiment of the present invention co-selection utilizing the system of the present invention together with one or more different selection system(s) (e.g. antibiotic resistant selection systems such as neo/G418) can be applied to further improve the performance. Besides further eukaryotic selectable markers, allowing the selection of eukaryotic host cells, also prokaryotic selectable markers can be used, which allow the selection in eukaryotic host cells. Examples of respective prokaryotic selectable markers are markers which provide a resistance to antibiotics such as e.g. ampicillin, kanamycin, tetracycline and/or chloramphenicol.

Vectors used for introducing the polynucleotides into the host cells usually contain transcriptional control elements suitable to drive transcription such as e.g. promoters, enhancers, polyadenylation signals, transcription pausing or termination signals as element of an expression cassette. If the desired product is a protein, suitable translational control elements are preferably included in the vector and operably linked to the polynucleotides to be expressed, such as e.g. 5' untranslated regions leading to 5' cap structures suitable for recruiting ribosomes and stop codons to terminate the translation process. In particular, the polynucleotide serving as the selectable marker genes as well as the polynucleotide encoding the product of interest can be transcribed under the control of transcription elements present in appropriate promoters. The resultant transcripts of the selectable marker genes and that of the product of interest harbour functional translation elements that facilitate substantial levels of protein expression (i.e. translation) and proper translation termination. A functional expression unit, capable of properly driving the expression of an incorporated polynucleotide is also referred to as an "expression cassette" herein.

The expression vector or combination of expression vectors according to the present invention used for introducing the polynucleotides into the eukaryotic host cells may comprise at least one promoter and/or promoter/enhancer element as element of an expression cassette. Although the physical boundaries between these two control elements are not always clear, the term "promoter" usually refers to a site on the nucleic acid molecule to which an RNA polymerase and/or any associated factors binds and at which transcription is initiated. Enhancers potentiate promoter activity, temporally as well as spatially. Many promoters are transcriptionally active in a wide range of cell types. Promoters can be divided in two classes, those that function constitutively and those that are regulated by induction or derepression. Both classes are suitable for the teachings of the present invention. Promoters used for high-level production of polypeptides in mammalian cells should be strong and preferably active in a wide range of cell types.

Strong constitutive promoters which drive expression in many cell types include but are not limited to the adenovirus major late promoter, the human cytomegalovirus immediate early promoter, the SV40 and Rous Sarcoma virus promoter, and the murine 3-phosphoglycerate kinase promoter, EF1a. Good results are achieved with the expression vector of the present invention when the promoter and/or enhancer is either obtained from CMV and/or SV40. The transcription promoters can be selected from the group consisting of an SV40 promoter, a CMV promoter, an EF1alpha promoter, a RSV promoter, a BROAD3 promoter, a murine rosa 26 promoter, a pCEFL promoter and a β-actin promoter.

Preferably, the polynucleotide encoding the product of interest and the polynucleotide encoding the DHFR enzyme are under the control of distinct transcription promoters. In general, a promoter capable of promoting expression, in particular transcription, of the essential polynucleotides in a eukaryotic host cell will be suitable. The distinct transcription promoters driving the expression from the polynucleotides can be the same or different.

According to one embodiment, a stronger promoter and/or enhancer is used for driving the expression of the polynucleotide encoding the product of interest than for driving the expression of the polynucleotide encoding the DHFR enzyme and/or the additional selectable markers if present. This arrangement has the effect that more transcript is generated for the product of interest than for the selectable markers. It is advantageous that the production of the product of interest is dominant over the production of the selectable markers, since the individual cell capacity for producing heterologous products is not unlimited and should thus be focused to the product of interest. Furthermore, the selection process only occurs at the initial stages of establishing an expression cell line, which then constantly produces the product of interest. Thus, it is advantageous to focus the resources of the cells to the expression/production of the product of interest. Furthermore, using a less strong promoter for expressing the selectable marker(s), in particular DHFR, further increases the selection pressure and thus allows the use of lower concentrations of DHFR inhibitors in the selective culture medium.

According to one embodiment, the promoter driving the expression of the polynucleotide encoding the product of interest is a CMV promoter and the promoter driving the expression of the polynucleotide encoding the DHFR enzyme is a SV40 promoter. The CMV promoter is known to be one of the strongest promoters available for mammalian expression and leads to a very good expression rate. It is considered to give significantly more transcript than the SV40 promoter.

According to a further embodiment, the polynucleotide encoding the product of interest and the polynucleotide encoding the DHFR enzyme are under the control of the same transcription promoter and are thus expressed from one expression cassette. Suitable promoters are described above. In this embodiment, one long transcript is obtained from the respective expression cassette that is under the control of said transcription promoter. According to one embodiment, at least one IRES element is functionally located between the polynucleotide encoding the product of interest and/or the polynucleotide encoding the DHFR enzyme. Thereby, it is ensured that separate translation products are obtained from said transcript.

The expression cassette may comprise an appropriate transcription termination site. This, as continued transcription from an upstream promoter through a second transcription unit may inhibit the function of the downstream promoter, a phenomenon known as promoter occlusion or transcriptional interference. This event has been described in both prokaryotes and eukaryotes. The proper placement of transcriptional termination signals between two transcription units can prevent promoter occlusion. Transcription termination sites are well characterized and their incorporation in expression vectors has been shown to have multiple beneficial effects on gene expression.

The host cell used is a eukaryotic, in particular a mammalian host cell. Most eukaryotic nascent mRNAs possess a poly A tail at their 3' end which is added during a complex process that involves cleavage of the primary transcript and a coupled polyadenylation reaction. The polyA tail is advantageous for mRNA stability and transferability. Hence, the expression cassettes for expressing the polynucleotides encoding the product of interest and the DHFR enzyme usually comprise a polyadenylation site suitable for transcription termination and polyadenylation. There are several efficient polyA signals that can be used in mammalian expression vectors, including those derived from bovine growth hormone (bgh), mouse beta-globin, the SV40 early transcription unit and the Herpes simplex virus thymidine kinase gene. However, also synthetic polyadenylation sites are known (see e.g. the pCl-neo expression vector of Promega which is based on Levitt el al, 1989, Genes Dev. 3, (7): 1019-1025). The polyadenylation site can be selected from the group consisting of SV40polyA site, such as the SV40 late and early poly-A site (see e.g. plasmid pSV2-DHFR as described in Subramani et al, 1981, Mol. Cell. Biol. 854-864), a synthetic polyA site (see e.g. the pCl-neo expression vector of Promega which is based on Levitt el al, 1989, Genes Dev. 3, (7): 1019-1025) and a bgh polyA site (bovine growth hormone).

Furthermore, an expression cassette comprising the polynucleotide encoding the product of interest and the polynucleotide encoding the DHFR enzyme may comprise at least one intron. This embodiment is particularly suitable when a mammalian host cell is used for expression. Most genes from higher eukaryotes contain introns which are removed during RNA processing. Respective constructs are expressed more efficiently in transgenic systems than identical constructs lacking introns. Usually, introns are placed at the 5' end of the open reading frame but may also be placed at the 3' end. Accordingly, an intron may be comprised in the expression cassette(s) to increase the expression rate. Said intron may be located between the promoter and or promoter/enhancer element(s) and the 5' end of the open reading frame of the polynucleotide to be expressed. Several suitable introns are known in the state of the art that can be used in conjunction with the present invention.

According to one embodiment, the intron used in the expression cassettes for expressing the product of interest, is a synthetic intron such as the SIS or the RK intron. The RK intron is a strong synthetic intron which is preferably placed before the ATG start codon of the gene of interest. The RK intron consists of the intron donor splice site of the CMV promoter and the acceptor splice site of the mouse IgG Heavy chain variable region (see e.g. Eaton et al., 1986, Biochemistry 25, 8343-8347, Neuberger et al., 1983, EMBO J. 2(8), 1373-1378; it can be obtained from the pRK-5 vector (BD PharMingen)).

An expression vector comprising the polynucleotides and/or expression cassettes as described above can be transfected into the host cell in its circular form. Supercoiled vector molecules usually will be converted into linear molecules within the nucleus due to the activity of endo- and exonucleases. However, linearization of the expression vector before transfection often improves the efficiency of a stable transfection. This also as the point of linearization may be controlled if the expression vector is linearized prior to transfection. Hence, according to one embodiment of the present invention the expression vector or combination of at least two expression vectors comprises at least one predefined restriction site, which can be used for linearization of the vector(s) prior to transfection. According to one embodiment, the linearization site is arranged such, that upon linearization, the polynucleotide encoding the DHFR enzyme is located 5' of the polynucleotide encoding the product of interest. This arrangement is advantageous for gene amplification. In case a prokaryotic selectable marker is additionally used, the polynucleotide encoding said prokaryotic marker is located 3' of the polynucleotide encoding the product of interest. This has the effect that the prokaryotic selection marker gene is 3' and thus "outside" of the "mammalian" parts of the linearized vector nucleic acid. This arrangement is favourable since prokaryotic genes are presumably not advantageous for mammalian expression as prokaryotic sequences may lead to increased methylation or other silencing effects in the mammalian cells.

The polynucleotide encoding a product of interest and the polynucleotide encoding the DHFR enzyme are preferably stably introduced into said host cell. The stable introduction respectively transfection is advantageous for establishing of expression cell lines and in particular for the large scale and accordingly industrial production of the product of interest.

There are several appropriate methods known in the prior art for introducing polynucleotides and expression vectors into eukaryotic host cells, including mammalian host cells. Respective methods include but are not limited to calcium phosphate transfection, electroporation, lipofection, biolistic- and polymer-mediated genes transfer. Besides traditional random integration based methods also recombination mediated approaches can be used to transfer the polynucleotide encoding the product of interest and the polynucleotides encoding a DHFR enzyme into the host cell genome. Such recombination methods may include use of site specific recombinases like Cre, Flp or ΦC31 (see e.g. Oumard et al, Cytotechnology (2006) 50: 93-108) which can mediate directed insertion of transgenes. Alternatively, the mechanism of homologous recombination might be used to insert said polynucleotides (reviewed in Sorrell et al, Biotechnology Advances 23 (2005) 431-469). Recombination based gene insertion allows to minimize the number of elements to be included in the heterologous nucleic acid that is transferred/introduced to the host cell. For example, an insertion locus might be used that already provides promoter and poly-A site (exogenous or endogenous) such that only the remaining elements (e.g. the polynucleotide encoding the product of interest and the polynucleotide encoding the DHFR enzyme needs to be transferred/transfected to the host cell. Embodiments of a suitable expression vector or combination of expression vectors according to the present invention as well as suitable host cells are described in detail above; we refer to the above disclosure.

In case a further selectable marker is used in addition to the DHFR enzyme, the selective conditions for said selectable marker can be applied prior to applying the selective conditions for the DHFR enzyme. E.g. in case the neomycin phosphotransferase gene (neo) is used as additional selectable marker, the cells can be grown first in a medium e.g. containing G418 in order to select cells that have incorporated the expression vector(s) according to the present invention.

The strategy of the present invention to use a limiting concentration of folate in the selective culture medium in addition to a DHFR selectable marker has the advantage that a very high stringency is obtained even if lower DHFR inhibitor concentrations are used. The productivity of the cell population surviving these novel selection conditions is remarkably increased. The examples have shown that the host cells obtained after the selection method produce the product of interest with a high yield. Also the average productivity of the individual host cells is increased. Thus, chances are improved to find high producer clones with lower screening efforts. Thus, the selection system according to the present invention is superior to selection systems used in the prior art. In particular host cells are obtained, which have a higher productivity compared to the use of the respective selectable markers alone. Thus, due to the higher stringency of the selection conditions, the selection procedure is optimized.

Cells obtained as a result of the stringent screening/selection procedure of the present invention will generally be isolated and may be enriched from non-selected cells of the original cell population. They can be isolated and cultured as individual cells. They can also be used in one or more additional rounds of selection, optionally for additional qualitative or quantitative analysis, or can be used e.g. in development of a cell line for protein production. According to one embodiment, an enriched population of producing host cells selected as described above is directly used as population for the production of the polypeptide of interest with a good yield. Preferably, a host cell is selected which stably expresses the product of interest. The advantages of a stable transfection/expression are described in detail above. We refer to the above disclosure.

Also provided is a method for producing a product of interest, comprising at least the following steps:
 (a) performing the selection method according to the present invention for selecting at least one eukaryotic host cell expressing the product of interest; and
 (b) culturing at least one selected eukaryotic host cell under conditions that allow for the expression of the product of interest.

As the selection method according to the present inventions allows the identification of high producing cell clones, said selection system is an important and integral part of the production process. The expressed product of interest may be obtained by disrupting the host cells. The polypeptides may also be expressed, e.g. secreted into the culture medium and can be obtained therefrom. Also combinations of the respective methods are possible. According to one embodiment, said host cells are cultured under serum-free conditions.

Thereby, products, in particular polypeptides, can be produced and obtained/isolated efficiently with high yield. The obtained product may also be subject to further processing steps such as e.g. purification and/or modification steps. Accordingly, the method for producing the product of interest may comprise at least one of the following steps:
 isolating the product of interest from said cell culture medium and/or from said host cell; and/or
 processing the isolated product of interest.

The product of interest, for example a polypeptide, produced in accordance with the invention may be recovered and optionally further processed, e.g. further purified, isolated and/or modified by methods known in the art. For example, the product may be recovered from the nutrient medium by conventional procedures including, but not limited to, centrifugation, filtration, ultra-filtration, extraction or precipitation. Purification may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction.

The product of interest can be any biological product capable of being produced by transcription, translation or any other event of expression of the genetic information encoded by said polynucleotide. In this respect, the product will be an expression product. The product of interest may be selected from the group consisting of polypeptides, nucleic acids, in particular RNA or DNA. The product can be a pharmaceutically or therapeutically active compound, or a research tool to be utilized in assays and the like. In a particularly preferred embodiment, the product is a polypeptide, preferably a pharmaceutically or therapeutically active polypeptide, or a research tool to be utilized in diagnostic or other assays and the like. A polypeptide is accordingly not limited to any particular protein or group of proteins, but may on the contrary be any protein, of any size, function or origin, which one desires to select and/or express by the methods described herein. Accordingly, several different polypeptides of interest may be expressed/produced. As is outlined above, the term polypeptides include proteins and/or peptides of any activity or bioactivity, including e.g. bioactive polypeptides such as enzymatic proteins or peptides (e.g. proteases, kinases, phosphatases), receptor proteins or peptides, transporter proteins or peptides, bactericidal and/or endotoxin-binding proteins, structural proteins or peptides, immune polypeptides, toxins, antibiotics, hormones, growth factors, vaccines or the like. Said polypeptide may be selected from the group consisting of peptide hormones, interleukins, tissue plasminogen activators, cytokines, immunoglobulins, in particular antibodies or functional antibody fragments or variants thereof. In a most preferred embodiment the polypeptide is an immunoglobulin molecule or antibody, or a functional variant thereof, for example a chimeric, or a partly or totally humanized antibody. Such an antibody can be a diagnostic antibody, or a pharmaceutically or therapeutically active antibody.

Also provided is a product obtained by a method according to the present invention as defined above and in the claims. Said product is preferably a polypeptide, in particular an immunoglobulin molecule or a functional fragment thereof.

According to one embodiment, the present invention also provides a selective culture medium comprising folate in a limiting concentration and at least one inhibitor of DHFR. Preferably, said selective culture medium has one or more of the following characteristics:
 (a) it comprises folate, preferably folic acid, in a concentration selected from:
  (aa) 500 nM or less;
  (bb) 250 nM or less;
  (cc) 150 nM or less;
  (dd) 100 nM or less;
  (ee) 75 nM or less;
  (ff) 50 nM or less;

(gg) 25 nM or less, and/or
(hh) 15 nM or less;
and/or
(b) it comprises folate, preferably folic acid, in a concentration range selected from
(aa) 0.1 nM-500 nM;
(bb) 0.1 nM-250 nM, preferably 2.5 nM-250 nM or 5 or 10 nM-250 nM;
(cc) 0.1 nM-150 nM, preferably 2.5 nM-150 nM or 5 or 10 nM-150 nM;
(dd) 1 nM-100 nM; preferably 2.5 nM-100 nM or 5 or 10 nM-100 nM;
(ee) 1 nM-75 nM; preferably 2.5 nM-75 nM or 5 or 10 nM-75 nM;
(ff) 1 nM-50 nM;
(gg) 2.5 nM-50 nM; and/or
(hh) 12.5 nM-50 nM
and/or
(c) it comprises the DHFR inhibitor, which is preferably an antifolate, in a concentration selected from
(aa) 500 nM or less;
(bb) 400 nM or less;
(cc) 300 nM or less;
(dd) 250 nM or less;
(ee) 200 nM or less;
(ff) 150 nM or less; and/or
(gg) 100 nM or less;
and/or
(d) it comprises the DHFR inhibitor, which is preferably an antifolate and more preferred MTX, in a concentration selected from
(aa) 1 nM-500 nM;
(bb) 10 nM-200 nM;
(cc) 10 nM-150 nM; and/or
(dd) 10 nM-100 nM.

The indicated concentrations and concentration ranges for the folate and the DHFR inhibitor can be combined with each other. The advantages and further preferred embodiments of concentration ranges and suitable embodiments for folates and antifolates in the selective culture medium were outlined in detail above in conjunction with the selection method according to the present invention; it is referred to the above disclosure. Said selective culture medium can be used in conjunction with the selection system of the present invention.

The full contents of the texts and documents as mentioned herein are incorporated herein by reference and thus form part of the present disclosure.

The following examples serve to illustrate the present invention without in any way limiting the scope thereof. In particular, the examples relate to preferred embodiments of the present invention.

EXAMPLES

In general, suitable materials, such as reagents, are familiar to the skilled person, commercially available and can be used in accordance with the manufacturer's instructions. The experiments were performed as described.

A transfection experiment in CHO cells is done using an expression vector containing expression cassettes for expressing a monoclonal antibody as product of interest. As selectable markers, a G418 resistence gene (NEO) and a DHFR gene are present on the expression vector in separate expression cassettes. This experiment demonstrates that the selection with reduced MTX amounts under low folic acid conditions yields high producing cell populations. As reference, standard selection conditions for DHFR are used, which use higher MTX concentrations and folic acid in non-limiting amounts.

Example I

DHFR and Limiting Concentrations of Folic Acid 1.1. The Expression Vector

The expression vector is a mammalian expression vector comprising the following decisive elements, which are arranged in the same orientation on the expression vector:

CMV promoter/enhancer
Intron
Polynucleotide encoding the antibody light chain
Multiple cloning site
SV40 poly A site
CMV promoter/enhancer
Intron
Polynucleotide encoding the antibody heavy chain
Multiple cloning site
SV40 poly A site
SV40 enhancer/promoter
Neomycin phosphotransferase (neo)
Poly A site (synthetic)
Ampicillin resistance gene
SV40 promoter
DHFR mutant gene being less sensible to MTX than the DHFR wildtype
Intron
Poly A site 1.2. Transfection and Selection of CHO-cells Cell cultivation, transfection and screening is carried out in shake flasks using a suspension of growing CHO cells in a culture medium appropriate for CHO cells without FCS. Cells were transfected with the expression vector by electroporation. In order to reduce intracellular folic acid reservoirs in the host cells and to prevent co-transfer of folic acid from the pre-culture medium to the selection medium, cells are passaged to folic acid free medium or medium with reduced folic acid content (e.g. 50 nM) prior to the transfection and selection. Depending on the cell viability, a first selection step is started 24-48 h after transfection by adding G418 and MTX containing selective culture medium to the cells. In a first selection step, three different MTX (2.5, 5 and 10 nM) and folic acid concentrations (12.5, 25 and 50 nM) are tested. As reference, a culture medium is used comprising non-limiting amounts of folic acid, here 11.3 µM—which corresponds to a standard concentration in the culture medium).

As soon as cells recover to a viability of above 80%, a second selection step is applied by passaging the cells to G418 free medium containing the same amount of folic acid as in the first selection step but 10 times as much MTX (i.e. 25, 50 and 100 nM). In case of the reference culture conditions, 500 nM MTX is added to the cells.

1.3. Determination of Pool Productivity

Productivity of the selected cell populations is analyzed after the first and final selection steps via overgrown shake flask batch cultures in a medium containing non-limiting amounts of folic acid (11.3 µM) without G418, but containing MTX in the same concentration as in the respective selection medium.

Batch cultures are seeded in a shake flask having 250 mL capacity with 50 mL working volume and are cultivated in a shaker cabinet (not humidified) at 150 rpm and 10% CO2. Viability of cells have to be >90% when starting the assay.

The seeding cell density is usually about $2 \times 10^5$ c/mL. Titer determination takes place at day 13. Antibody titers in the cell culture supernatant are determined by protein-A HPLC 13 days after starting the culture.

1.4. Results

To evaluate the stringency of dhfr/MTX selection under limiting folic acid concentrations, transfection of a DHFR vector expression for expressing a monoclonal antibody is done in this example I. The vector also contains a G418 resistance gene (see above). First, transfected cell populations are selected by adding G418 and different concentrations of MTX at different concentrations of folic acid. This initial first selection step should help to kill untransfected cells and in parallel force the cells to consume intracellular folic acid reservoirs before higher stringency is applied in the second selection step. Under these conditions all transfected cell populations usually recovered and productivity is assessed as described above.

Table 1 summarizes the productivity results obtained:

TABLE 1

Productivity of cell populations after 1st selection step.

| Selection Medium | Productivity mAb (mg/L) |
|---|---|
| I. Test series without (w/o) MTX and low folic acid (FA) concentrations (12.5 nM, 25 nM and 50 nM) | |
| +0.8 g/L G418<br>+12.5 nM FA<br>+w/o MTX | 16 |
| +0.8 g/L G418<br>+25 nM FA<br>+w/o MTX | 12 |
| +0.8 g/L G418<br>+50 nM FA<br>+w/o MTX | 17 |
| II. Test series with a low MTX concentration (2.5 nM) and low folic acid (FA) concentrations (12.5 nM, 25 nM and 50 nM) | |
| +0.8 g/L G418<br>+12.5 nM FA<br>+2.5 nM MTX | 12 |
| +0.8 g/L G418<br>+25 nM FA<br>+2.5 nM MTX | 17 |
| +0.8 g/L G418<br>+50 nM FA<br>+2.5 nM MTX | 11 |
| III. Test series with a low MTX concentration (5 nM) and low folic acid (FA) concentrations (12.5 nM, 25 nM and 50 nM) | |
| +0.8 g/L G418<br>+12.5 nM FA<br>+5 nM MTX | 12 |
| +0.8 g/L G418<br>+25 nM FA<br>+5 nM MTX | 33 |
| +0.8 g/L G418<br>+50 nM FA<br>+5 nM MTX | 16 |
| IV. Test series with a low MTX concentration (10 nM) and low folic acid (FA) concentrations (12.5 nM, 25 nM and 50 nM) | |
| +0.8 g/L G418<br>+12.5 nM FA<br>+10 nM MTX | 205 |
| +0.8 g/L G418<br>+25 nM FA<br>+10 nM MTX | 30 |
| +0.8 g/L G418<br>+50 nM FA<br>+10 nM MTX | 23 |

TABLE 1-continued

Productivity of cell populations after 1st selection step.

| Selection Medium | Productivity mAb (mg/L) |
|---|---|
| V. Test series with non-limiting concentrations of folic acid (FA) (11.3 µM) and different MTX concentrations (0; 2; 2.5; 5 and 10 nM) | |
| +0.8 g/L G418<br>+11.3 µM FA<br>+w/o MTX | 16 |
| +0.8 g/L G418<br>+11.3 µM FA<br>+2.5 nM MTX | 11 |
| +0.8 g/L G418<br>+11.3 µM FA<br>+5 nM MTX | 16 |
| +0.8 g/L G418<br>+11.3 µM FA<br>+10 nM MTX | 11 |

Transfected cells selected in G418 and MTX containing medium with different folic acid concentrations are analyzed in shake flask batch cultures. At day 13 of the culture, samples of the culture medium are taken and are analyzed for antibody content by Protein-A HPLC.

The results show that all cell populations produce antibodies. Addition of less than 10 nM MTX does not show much effect on the cells even at low folic acid concentrations. The concentration of produced antibody is comparable to selection in the absence of MTX. However, when using 10 nM MTX in the first selection step, productivity of cells at low folic acid concentrations increase significantly and in a concentration dependent manner. After selection with the lowest folic acid concentration (12.5 nM) and 10 nM MTX, the productivity of the cells is found to be more than 10 fold higher compared to medium with standard folic acid concentration.

To further increase selection stringency, the next step is to remove G418 but to increase MTX concentration in the culture medium by a factor of 10, while keeping the folic acid concentration used in the first selection step. In case of the reference, MTX is added at a high concentration as is common in the prior art, here at 500 nM. Under these conditions, viability of the cells of many transfected populations dramatically drops and stays at low levels so that not all of them can be recovered. Cell populations that could be recovered are further expanded and productivity is analyzed (Tab. 2).

TABLE 2

Productivity of cell populations after 2nd selection step.

| Selection Medium | Productivity mAb (mg/L |
|---|---|
| Test series with 10 nM MTX and low folic acid (FA) concentrations (12.5 nM, 25 nM and 50 nM) | |
| +w/o G418<br>+12.5 nM FA<br>+10 nM MTX | No recovery |
| +w/o G418<br>+25 nM FA<br>+10 nM MTX | 19 |
| +w/o G418<br>+50 nM FA<br>+10 nM MTX | 15 |

TABLE 2-continued

Productivity of cell populations after 2nd selection step.

| Selection Medium | Productivity mAb (mg/L) |
|---|---|
| Test series with 25 nM MTX and low folic acid (FA) concentrations (12.5 nM, 25 nM and 50 nM) | |
| +w/o G418<br>+12.5 nM FA<br>+25 nM MTX | No recovery |
| +w/o G418<br>+25 nM FA<br>+25 nM MTX | No recovery |
| +w/o G418<br>+50 nM FA<br>+25 nM MTX | 20 |
| Test series with 50 mM MTX and low folic acid (FA) concentrations (12.5 nM, 25 nM and 50 nM) | |
| +w/o G418<br>+12.5 nM FA<br>+50 nM MTX | No recovery |
| +w/o G418<br>+25 nM FA<br>+50 nM MTX | No recovery |
| +w/o G418<br>+50 nM FA<br>+50 nM MTX | 20 |
| Test series with 100 nM MTX and low folic acid (FA) concentrations (12.5 nM, 25 nM and 50 nM) | |
| +w/o G418<br>+12.5 nM FA<br>+100 nM MTX | 277 |
| +w/o G418<br>+25 nM FA<br>+100 nM MTX | 131 |
| +w/o G418<br>+50 nM FA<br>+100 nM MTX | 15 |
| Test series with non-limiting concentration of folic acid (FA) (11.3 µM) and a MTX concentration of 500 nM | |
| +w/o G418<br>+11.3 µM FA<br>+500 nM MTX | 31 |
| +w/o G418<br>+11.3 µM FA<br>+500 nM MTX | 26 |
| +w/o G418<br>+11.3 µM FA<br>+500 nM MTX | 21 |
| +w/o G418<br>+11.3 µM FA<br>+500 nM MTX | 25 |

G418 and MTX selected cell populations are further selected by increasing the MTX concentration. Recovered populations are analyzed in shake flask batch cultures. At day 13 of the culture, samples of the culture medium are taken and analyzed for antibody content by Protein-A HPLC.

The productivity of the reference cell populations (500 nM MTX, 11.3 µM FA) after this selection step increase to approximately 25-30 mg/L. No benefit is seen at MTX concentrations below 100 nM. However, when using 100 nM MTX in combination with a low folic acid content (12.5 or 25 nM) productivities are up to 277 mg/L and thus 10 times higher then the reference even though low MTX concentrations are used for amplification/selection.

Thus, using DHFR as selectable marker in combination with limiting folic acid concentration in the selective medium generates cells highly overexpressing a protein of interest even at low DHFR inhibitor concentrations. The results also show that this combination is superior to conventional selection systems (e.g. DHFR/G418 using standard folic acid concentration in the selective medium).

Example II

Large Scale Production of Polypeptides with Transfected CHO Cells

The production of polypeptides in large scale can be done for example in wave, glass or stainless steel bioreactors. For that purpose the cells are expanded, usually starting from a single frozen vial, for example a vial from a Master Cell Bank. The cells are thawed and expanded through several steps. Bioreactors of different scale are inoculated with appropriate amounts of cells. The cell density can be increased by adding feed solutions and additives to the bioreactor. Cells are kept at a high viability for a prolonged time. Product concentrations in the reactor ranging from a few hundred milligrams per liter up to several grams per litre are achieved in the large scale. Purification can be done by standard chromatography methodology, which can include affinity, ione exchange, hydrophobic interaction or size exclusion chromatography steps. The size of the bioreactor can be up to several thousand litres volume in the final scale (see also e.g. F. Wurm, Nature Biotechnology Vol. 22, 11, 2004, 1393-1398).

The invention claimed is:

1. A method for selecting at least one eukaryotic host cell expressing a product of interest, comprising at least the following steps:
    (a) providing a plurality of eukaryotic host cells, wherein cellular viability of said host cells is dependent upon folate uptake, wherein said eukaryotic host cells comprise at least
        (i) an introduced polynucleotide encoding a product of interest and
        (ii) an introduced polynucleotide encoding a DHFR enzyme;
    (b) culturing said plurality of eukaryotic host cells in a selective culture medium comprising at least an inhibitor of DHFR and folate in a limiting concentration;
    (c) selecting at least one eukaryotic host cell expressing the product of interest.

2. The method according to claim 1, wherein the selective culture medium comprises the DHFR inhibitor in a concentration of 500 nM or less and a folate in a concentration of 500 nM or less.

3. The method according to claim 1, wherein the selective culture medium comprises the DHFR inhibitor in a concentration of 200 nM or less and it comprises a folate in a concentration of 2.5 nM-100 nM.

4. The method according to claim 1 wherein the folate is folic acid in a concentration of 12.5 nM-50 nM and wherein the DHFR inhibitor is MTX in a concentration of 10 nM-100 nM.

5. The method according to claim 1 wherein the DHFR enzyme is a DHFR enzyme having a lower sensitivity to a DHFR inhibitor than the DHFR enzyme endogenously expressed by the host cell.

6. The method according to claim 1 wherein said eukaryotic host cell is a CHO host cell.

7. The method according to claim 1 wherein a DHFR $^+$(plus) host cell is used in conjunction with an introduced DHFR enzyme that is less sensitive to MTX than the DHFR enzyme endogenously expressed by the host cell.

8. The method according to claim 1 wherein the polynucleotide encoding a product of interest and the polynucleotide encoding a DHFR enzyme have been introduced by at least one expression vector.

9. The method according to, claim 1 wherein the host cell comprises at least two introduced polynucleotides encoding a product of interest.

10. The method according to claim 1, wherein the introduced polynucleotide(s) encoding the product of interest and the introduced polynucleotide encoding the DHFR enzyme are comprised in different expression cassettes and wherein the expression cassette(s) for driving the expression of the polynucleotide(s) encoding the product of interest comprises a stronger promoter and enhancer than the expression cassette for driving the expression of the polynucleotide encoding the DHFR enzyme.

11. The method according to claim 2 wherein the DHFR enzyme is a DHFR enzyme having a lower sensitivity to a DHFR inhibitor than the DHFR enzyme endogenously expressed by the host cell.

12. The method according to claim 1 wherein said eukaryotic host cell is a DHFR $^+$(plus) cell.

13. The method according to claim 2 wherein a DHFR $^+$(plus) host cell is used in conjunction with an introduced DHFR enzyme that is less sensitive to MTX than the DHFR enzyme endogenously expressed by the host cell.

14. The method according to claim 1 wherein the host cell comprises at least two introduced polynucleotides encoding a product of interest, wherein at least one polynucleotide encodes the heavy chain of an immunoglobulin molecule and the other polynucleotide encodes the light chain of an immunoglobulin molecule.

15. The method according to claim 1 wherein the introduced polynucleotide(s) encoding the product of interest and the introduced polynucleotide encoding the DHFR enzyme are comprised in different expression cassettes and wherein the expression cassette(s) for driving the expression of the polynucleotide(s) encoding the product of interest comprises a stronger promoter or enhancer than the expression cassette for driving the expression of the polynucleotide encoding the DHFR enzyme.

* * * * *